Figure 1:
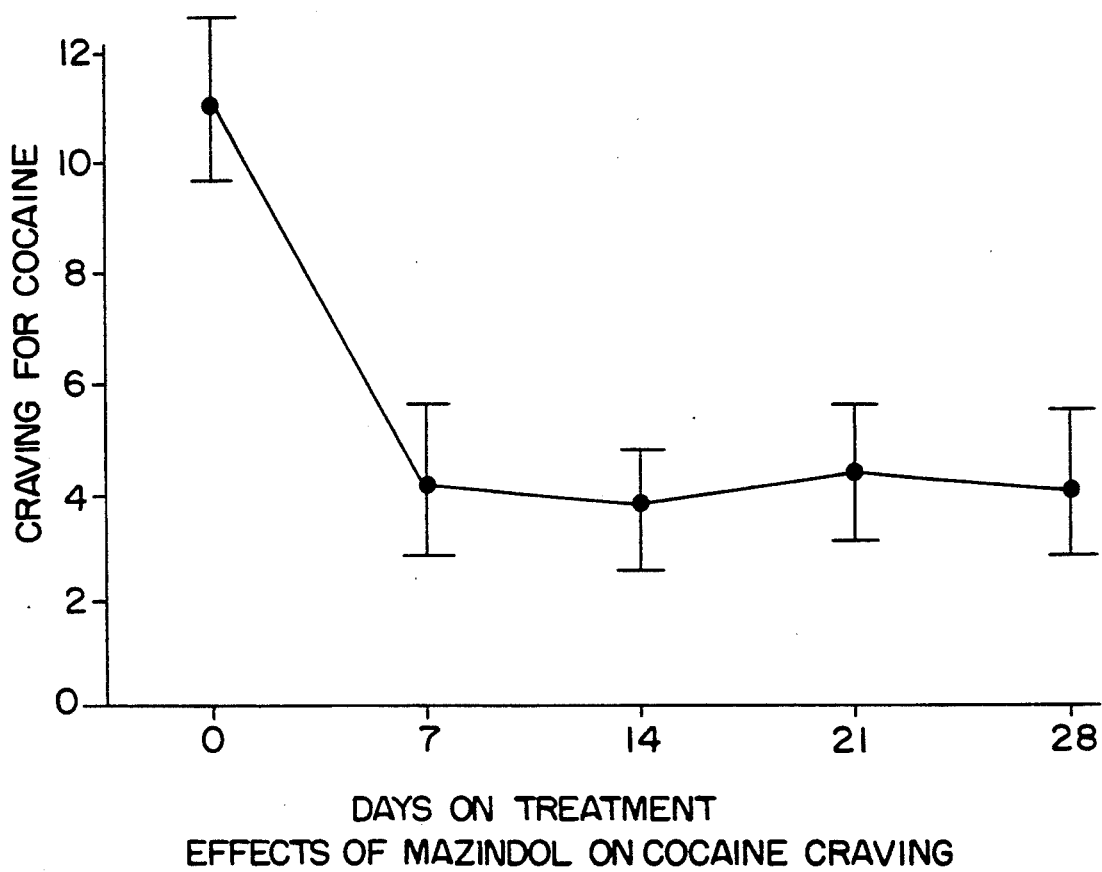

United States Patent [19]

Berger

[11] Patent Number: 5,217,987

[45] Date of Patent: Jun. 8, 1993

[54] DOPAMINE UPTAKE INHIBITORS IN REDUCING SUBSTANCE ABUSE AND/OR CRAVING

[76] Inventor: Stephen P. Berger, 1 Ewing Ct., Bethesda, Md. 20817

[21] Appl. No.: 474,618

[22] Filed: Feb. 5, 1990

Related U.S. Application Data

[63] Continuation-in-part of Ser. No. 428,307, Oct. 30, 1989, abandoned.

[51] Int. Cl.[5] ............................................. A61K 31/40
[52] U.S. Cl. .................................... 514/416; 514/255; 514/304; 514/366; 514/506; 514/629
[58] Field of Search ............... 514/506, 810, 811, 812, 514/813, 255, 304, 366, 629, 416

[56] References Cited

U.S. PATENT DOCUMENTS

| | | | |
|---|---|---|---|
| 4,786,653 | 11/1988 | Golwyn | 514/654 |
| 4,919,916 | 4/1990 | Golwyn | 424/10 |
| 4,935,429 | 6/1990 | Dackis | 514/288 |

OTHER PUBLICATIONS

L. D. Chait et al., Reinforcing and Subjective Effects of Several Anorectics in Normal Human Volunteers; 1987 vol. 242 pp. 777-783.
Prog. Neuropsychopharmacol. & Biol. Psychiat. 1988 (12) 233-239, "Cocaine Self Administration Appears to be Mediated by DA Uptake Inhibition".
Lif Sci. 1979(24) 159-168, "The Central Stimulatory Action of Inhibitors of DA Uptake".
Eur. J. Pharmacol. 1986(126) 211-222, "High Affinity [3H]GBR 12783 Binding to a Specific Site Assoc. w/Neuronal DA Uptake Complex in the CNS".
"Dissociation of the Actions of Uptake Blockers on DA Overflow and Uptake in the Rat Nucleus Accumbens: In Vivo Voltammetric Data", AN=CA112(9):69849.
"Effects of Cocaine and Related Drugs in Nonhuman Primates", II AN=CA111(23):209081.
"Effects of Cocaine and Related Drugs in Nonhuman Primates", III AN=CA111(23) 209082.
"Circling induced by a DA Uptake Inhibitors", AN=CA91(7):49366.
F. H. Gawin et al., "An Open Trial of Mazindol to Treat Cocaine Craving in a Methadone Maintenance Clinic", Societ for Neuroscience 1988 Abstract Form, May 2, 1988.
The Lancet, Feb. 4, 1990, p. 283.
P. van der Zee et al., "Aryl 1,4-dialk(en)ylpiperazines as selective and very potent inhibitors of dopamine uptake", Eur. J. Med. Chem, Jul.-Aug. 1980-15, No. 4, pp. 363-370.
K. Kumor et al., "Effects of Bromocriptine Pretreatment on Subjective and Physiological Responses to IV Cocaine", Pharmacology Biochemistry and Behavior, vol. 33, pp. 829-837, Pergamon Press, plc. 1980.
Physician's Desk Reference, Edition 43, p. 1571, 1989.
Angel et al., Brain Research, 503, pp. 339-341 (1989).
Zaczek et al., The Journal of Pharmacology and Expeimental Therapeutics, vol. 257, pp. 830-835 (1991).
Jaffe et al., "Potential Toxic Interactions of Cocaine and Mazindol", The Lancet, p. 111 (Jul. 8, 1989).

*Primary Examiner*—Frederick E. Waddell
*Assistant Examiner*—Frederick F. Tsung
*Attorney, Agent, or Firm*—Millen, White, Zelano & Branigan

[57] ABSTRACT

Mazindol and other nonreinforcing dopamine uptake inhibitors are effective to lessen craving for abused substances.

1 Claim, 1 Drawing Sheet ial application. This application is a continuation-in-part of U.S. Ser. No. 07/428,307 filed on Oct. 30, 1989, now abandoned, whose disclosure is entirely incorporated by reference herein.

DOPAMINE UPTAKE INHIBITORS IN REDUCING SUBSTANCE ABUSE AND/OR CRAVING

CROSS-REFERENCE TO RELATED APPLICATION

This application is a continuation-in-part of U.S. Ser. No. 07/428,307 filed on Oct. 30, 1989, now abandoned, whose disclosure is entirely incorporated by reference herein.

BACKGROUND OF THE INVENTION

This invention relates to methods for reducing substance abuse or even achieving abstinence therefrom and/or blocking substance-mediated euphoria and/or reducing or eliminating substance craving.

A major problem throughout the world is substance abuse, e.g., drug abuse, including cocaine abuse, heroin abuse, alcohol abuse, amphetamine abuse, nicotine abuse, etc. Many resources have been directed toward reducing or eliminating these problems and their enormous social costs. However, these remain largely ineffective.

For example, the current major pharmacological treatment for cocaine abuse and craving, desipramine, though somewhat effective, is limited by a delayed onset of two to three weeks. (Gawin, F. H, Kleber, H. D., "Cocaine abuse treatment: Open pilot trial with desipramine and lithium carbonate," *Arch. Gen. Psychiat.*, 42:903–910, 1984.) During this period, patients experience anticholinergic side effects such as dry mouth and blurry vision without therapeutic benefit; therefore, there is an initial high risk of patients dropping out of desipramine treatment. Moreover, several groups have reported that the direct dopamine agonist, amantadine, and the direct dopamine agonist, bromocriptine, are of use in the treatment of cocaine abuse. (Tennant, F. S., et al., "Double blind comparison of amantadine and bromocriptine for ambulatory withdrawal from cocaine dependence," *Arch. Int. Med.* 147:109–112, 1987.)

Similarly, various methods have been devised to reduce abuse of other substances such as those mentioned above, most notably smoking (nicotine). However, in all cases, the results are unsatisfactory and improvement is needed.

Mazindol is in widespread clinical use as an anorectic. Its minimal side effects include restlessness and insomnia. Because of its cocaine-like dopamine uptake inhibition, it is of use in both Parkinson's disease and narcolepsy. Although Parkinson's patients are notoriously sensitive to side effects, mazindol is a remarkably well tolerated drug. Out of twelve patients in a recent pilot study of mazindol for Parkinsonism, only two reported even mild side effects. (Delwaid, P. J., et al., "Mazindol in the treatment of Parkinson's disease," *Arch. Neurol.* 40:788–790, 1983.) In a recent report, unexpectedly, when given blindly to normal healthy adults, the oral clinical dose of mazindol was mildly dysphoric and free of abuse potential. (Chait, et al., "Reinforcing and Subjective Effects of Several Anorectics in Normal Human Volunteers," *J. Pharmaceutical Exp. Ther.*, 1987; 242, 777–83.) However, prior to this invention, mazindol has never been used clinically in managing substance abuse.

With respect to abused amphetamines, it is known preclinically that mazindol chemically blocks their reward effects. However, as usual, such preclinical studies are not reliably predictive of clinical results.

SUMMARY OF THE INVENTION

It has now been discovered that dopamine uptake inhibitors (e.g., that bind in a live human brain to a dopamine uptake protein) and which are not reinforcing after administration, are useful in reducing or eliminating substance craving and/or abuse.

Thus, this invention relates to a method of reducing cocaine craving and/or abuse in a patient who experiences episodes of cocaine craving comprising administering to the patient during a cocaine craving episode an amount of mazindol effective to lessen cocaine craving and/or abuse in the patient (when mazindol binds to the dopamine uptake carrier (protein) it is believed to prevent cocaine from binding to this protein);

a method of reducing cocaine craving and/or abuse in a patient who experiences episodes of cocaine craving comprising administering to the patient a dopamine uptake inhibitor that binds to the dopamine uptake protein in a live human brain (e.g., to the cocaine receptor) and is not reinforcing after said administering, in an amount effective to lessen cocaine craving and/or abuse in the patient, with the proviso that said dopamine uptake inhibitor is not mazindol; and a method of reducing substance craving and/or abuse in a patient who experiences episodes of craving said substance comprising administering to the patient a dopamine uptake inhibitor that binds in a live human brain to the dopamine uptake protein and is not reinforcing after said administering, in an amount effective to lessen craving and/or abuse of said substance in the patient, with the proviso that the craved and/or abused substance is not cocaine.

In preferred aspects, the craved and/or abused substance is cocaine, nicotine, heroin, alcohol, amphetamines, etc.; the nonreinforcing, dopamine uptake inhibitor used to reduce substance craving and/or abuse by suitable administration before, during or after craving is a GBR compound or mazindol, but also other compounds having the mentioned functionality, including benztropine or buprorion; and the administration is effected during an episode of craving for the substance. In general, the dopamine uptake inhibitors of this invention will function by binding to receptors on the dopamine uptake protein.

In another aspect, this invention relates to a method of reducing or blocking the euphoria caused in a patient by an abused substance comprising administering to the patient a dopamine uptake inhibitor that binds in a live human brain to a dopamine uptake protein and is not reinforcing after said administering, in an amount effective to reduce said euphoria. The same preferred aspects apply where applicable.

Various other objects, features and attendant advantages of the present invention will be more fully appreciated as the same becomes better understood when considered in conjunction with the accompanying drawings, and wherein FIG. 1 shows the results of an outpatient study of the effects of mazindol administration on craving for cocaine in cocaine abusers, as described in Example 1.

Like amantadine, mazindol is an indirect dopamine agonist. Preclinically, it shares more properties in common with cocaine than does amantadine.

Specifically, mazindol is a dopamine, norepinephrine and serotonin uptake inhibitor like cocaine, and it induces the same behavioral stereotypes and conditioned place preference as cocaine, and even substitutes for cocaine in self administration studies. Most notably in the striatum of the brain a common receptor on the dopamine uptake carrier has been proposed for both mazindol and cocaine, and the investigators propose that this receptor may mediate cocaine's reinforcing and abuse potential in man. (Ritz, et al., "Cocaine receptors on dopamine transporters are related to cocaine self-administration," *Science* 1219-1223, 1987.)

In this application, the term "substance abuse" has its conventional meaning, e.g., misuse of a "substance," e.g., a chemical compound, e.g., a drug. Typically, the substance is taken by a person due to a craving for the substance generated by prior use of the substance. The substance is "abused" in that it is used for gratification, producing effects not required or recommended for therapy. For most of the substances, the resultant high "use" of the substance produces many serious and adverse side effects such as those that are well known for the abused substances mentioned herein, both of a personal and a societal nature. Obviously, it is highly desired to reduce the number and/or intensity of episodes in which a person experiences a craving for the substance or, hopefully, to eliminate the craving episodes entirely.

The agents useful in the methods of this invention are those which are dopamine uptake inhibitors, which bind to the receptor for the substance in a live brain and which are not reinforcing by the chosen route of administration. Agents which are dopamine uptake inhibitors binding to the uptake protein for dopamine are known and/or can be chosen by standard pharmacological in vitro protocols, e.g., using brain samples, e.g., as disclosed in Janowsky et al., J. Neurochem., Vol. 46, pp. 1272-1276 (1986). These procedures can be modified and/or developed routinely for a given substance, particularly new abused substances. Routine clinical tests can thereafter be utilized to determine the clinical efficacy of a thus-chosen candidate agent.

The term "reinforcing," as used herein, has its standard meaning, e.g., and refers to, e.g., effects of a substance which cause self-administration thereof in animals or which support animal behavioral patterns paired with the substance or which cause a substance to be rated by addicts as possessing reinforcing characteristics in standard tests. The substances used in this invention are non-addictive. It is important to note that a substance can be reinforcing by one route of administration (e.g., injection) and not by another (e.g., orally). Thus, the term "reinforcing" refers to the results which occur by the route of administration used for the anticraving, blocking or other treatment of this invention. The lack of reinforcement can be conventionally determined using routine procedures.

The precise dosages utilized in the methods of this invention are not critical. Typically, effective dosages will be those amounts for which a candidate agent is effective for other uses of the agent, if any. Thus, mazindol can be utilized in dosages for which it is approved for administration for other purposes, such as anorectic treatment. The same is true for the GBR compounds (useful as antidepressants). For mazindol, see, e.g., the Physicians Desk Reference where suitable dosages are given. For an individual case, the usual considerations prevalent in the pharmaceutical industry will be employed to determine preferred precise dosages, including the state of health of the patient, the age, the body weight, the activity of the agent as indicated by the protocols mentioned above, and data gathered in preliminary clinical tests, etc. All modes of administration are applicable, including oral, injection, transdermal, etc.

For both the lessening of substance abuse and/or craving (e.g., number of craving episodes, intensity of craving episodes, etc.) and for blocking substance-induced euphoria, administration may be performed before, during, after and/or between craving episodes. Thus, the methods of this invention can be of both a prophylactic and therapeutic nature. It is particularly surprising that the administration can be performed during a craving episode with resultant effect on the particular craving episode involved.

Suitable agents for use in the methods of this invention which satisfy the functional criteria of being dopamine uptake inhibitors which bind in a live brain (e.g., human) to a dopamine uptake protein and being nonreinforcing after the particular mode of administration, include mazindol, GBR compounds (which are well known in the antidepressant field, for example), benztropine, buproprion, etc. Also useful are the compounds disclosed in Bogeso et al., J. Med. Chem., Vol. 28, p. 1817 (1985), e.g., Lu 19-005 (+)trans-3(3,4-dichlorophenyl)-N-methyl-1-indanamine. Methylphenidate (ridlin), for example, is not useful in this invention because it is a reinforcing dopamine uptake inhibitor. Also preferred are agents meeting the definition of appropriate dopamine uptake inhibitors per this application and which also have a higher affinity for the uptake protein than does the abused substance per se, as in the case of cocaine or any metabolite or other substance mediated thereby which binds to the uptake protein, e.g., those which are likely to bind to the protein more slowly but more tightly and for a longer period of time than the abused substance or metabolite or mediated substance. However, the invention is not limited to these preferred aspects, e.g., buproprion has a lower affinity than cocaine.

GBR compounds include 1-[2-(diphenylmethoxy)-ethyl]piperazines, optionally substituted, especially those wherein the piperazine is 4-substituted by, e.g., 4-(3-phenyl-2-prop(en)yl), and those wherein the diphenylmethoxy group is substituted by one or more strongly inductive groups having small volume analogous to those of van der Zee et al., Eur. J. Med. Chem. Chemica Therapeutica, July-Aug. 1980-15, No. 4, pp. 363-370, e.g., selected from those discussed in standard texts of organic chemistry, e.g., Morrison & Boyd, (*Organic Chemistry*, 4th Ed., New York Univ., 1983), and/or those wherein the solitary phenyl group on the 4-piperazine substituent is substituted by one or more substituents having a strong electron withdrawing effect and a small volume as defined above and, e.g., selected from those discussed in standard texts of organic chemistry, e.g., Morrison et al. A preferred agent is GBR 12921 (1-[2-(diphenylmethoxy)-ethyl]-4-(3-phenyl-2-propenyl)piperazine hydrochloride).

All routes of administration are applicable for this invention. However, oral administration is preferred.

Typical administration regimens for a given class of patients can involve various combinations of timing of administration as can be routinely determinable using conventional considerations. Thus, it is possible to administer one dose of a suitable agent at the same time every day and in addition have the patient self-administer additional doses during craving episodes during that day up to a maximum number of doses conventionally determinable. In general, higher doses will be useful in blocking the effect of an abused substance than in reducing the craving for it.

For a given patient, administration will generally continue until the number or severity of craving episodes diminishes to a point where abstinence from abuse of the substance can be maintained without the assistance of the methods of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, are hereby incorporated by reference.

EXAMPLES

EXAMPLE 1

The effect of mazindol on cocaine craving and use was examined in an open study of cocaine abusers (DSM-IIIR) in an outpatient methadone maintenance program. Patients were treated with 1-3 mg per day (titration based on side effects and effect on craving), the conventional anorectic dose. Craving was measured daily on a 20-point analogue scale. (Gawin, P. H., Kleber, H. D., "Cocaine abuse treatment: open pilot trial with desipramine and lithium carbonate," *Arch. Gen. Psychiatry*, 42:903-10, 1984.) Random urine screens were run weekly to verify abstinence.

On the first day of administration, mazindol significantly reduced craving for cocaine below baseline (t test; df=7, $p \leq 0.02$) and remained effective up to 28 days, the period of study (FIG. 1). Self-reported use also decreased with four patients achieving abstinence for at least 2 consecutive weeks during the study. No cocaine was found in these patients' urines. All patients who abused cocaine during the study reported a decrease in cocaine-induced euphoria, which they attributed to mazindol. No significant side-effects were reported with mazindol and all patients started on mazindol completed the study, unlike earlier open trials in the same clinic with bromocriptine or desipramine. In addition to reducing cocaine craving, reduced cigarette smoking and abstinence from cocaine were found. Smoking was reduced in patients not attempting to cease smoking.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of reducing cocaine craving in a human who experiences episodes of cocaine craving comprising administering to the human during a cocaine craving episode an amount of mazindol effective to lessen cocaine craving in the human.

* * * * *